United States Patent [19]

Lippa et al.

[11] Patent Number: 4,857,514

[45] Date of Patent: Aug. 15, 1989

[54] VIRUS INACTIVATION

[75] Inventors: Arnold S. Lippa, Franklin Lakes, N.J.; David I. Scheer, Branford, Conn.

[73] Assignee: Yeda Research and Development Company, Ltd., Rehovot, Israel

[21] Appl. No.: 776,918

[22] Filed: Sep. 17, 1985

[51] Int. Cl.$^4$ ............................................. A61K 31/685
[52] U.S. Cl. ...................................... 514/78; 514/885; 514/934
[58] Field of Search ........................... 514/78, 885, 934

[56] References Cited

U.S. PATENT DOCUMENTS 4,474,773 10/1984 Shinitzky et al. ...................... 514/78

OTHER PUBLICATIONS

Sarin et al., The New Eng. J. of Med., 313:1289–1290, 1985.
Moore et al., J. Virol., 27:320–329, 1978.
Omar Sattaur, *This Week*, New Scientist, (Feb. 7, 1985).
M. Popovic et al., *Science*, 224:497–500, (May 4, 1984).
H. Mitsuya et al., *Science*, 226:172–174, (Oct. 12, 1984).
R. Soave et al., *Anals of Internal Medicine*, 199:504–511, (Apr. 1984).
P. Sarin et al., *Journal of Clinical Immunology*, vol. 4, No. 6, pp. 415–423, (1984).
H. J. Alter et al., *Science*, 226:549–552.
Pal et al., *Biochemistry* 20: 530–539, (1981).
Moore et al., *Biochemistry* 16: 4708–4715, (1977).

*Primary Examiner*—John W. Rollins
*Attorney, Agent, or Firm*—Bernard, Rothwell & Brown

[57] ABSTRACT

A virus having a lipid-containing capsid, such as AIDS virus, is inactivated by contacting the virus with an inactivating amount of phosphatidyl choline. Such a virus can be inactivated in fluids such as virus-contaminated body fluids or derivatives, e.g., blood or blood derivatives. The phosphatidyl choline can be present in an Active Lipid (AL) composition further comprising neutral lipids and phosphatidyl ethanolamine. Phosphatidyl choline, and an AL composition containing same, is useful for the treatment or prophylaxis of Acquired Immune Deficiency Syndrome (AIDS) in mammals.

36 Claims, No Drawings

VIRUS INACTIVATION

BACKGROUND OF THE INVENTION

1. Field of the Invention

The present invention relates to a method for inactivating viruses having lipid-containing capsids, such as the virus responsible for Acquired Immune Deficiency Syndrome in humans.

2. Description of the Background Art

Acquired Immune Deficiency Syndrome (AIDS) has recently become a significant public health threat, although the disease was a little known condition only a few years ago.

AIDS is believed to be transmitted through contact with infected body fluids,, and the disease has rapidly spread among promiscuous homosexuals, intravenous drug abusers and hemophiliacs dependent upon clotting factor VIII.

In its fully developed form, AIDS is a disease characterized by a profound loss of immune T-cell function. T-cells are lymphocytes that are critical for the body's immune response to infection. The loss of immune T-cell function results in a spectrum of opportunistic infectious disease complications, including *Pneumocystis carinii* pneumonia, Herpes simplex, cytomegalovirus, candidiasis, cryptosporidosis, and the like.

Though most patients die from the infectious complication of AIDS, a subset develop a highly malignant tumor called Kaposi's Sarcoma, for which there is currently no effective form of treatment.

A significant breakthrough in AIDS research occurred in 1983-1984, when two groups independently isolated and identified a virus which is believed to be the causative agent of AIDS. A full description of the AIDS virus discovery is provided in Sattaur, O., *New Scientist*, Feb. 7, 1985, p. 3. A group in France, led by Luc Montaignier, first described a retrovirus Lymphoadenopathy Associated Virus (LAV) in May, 1983. A year later, an American group led by Robert Gallo described a virus isolated from AIDS patients that was ostensibly related to a class of viruses known as Human T-cell Leukemia Viruses (HTLV's), and named the virus HTLV-III. Determination of the complete nucleotide sequences of the genomes of the HTLV-III virus and the LAV virus demonstrated that they are variants of the same virus.

The AIDS virus (HTLV-III, LAV) is a member of a class of viruses known as "retroviruses", so-called because they possess an enzyme called reverse transcriptase that uses the viral RNA as a template for the synthesis of a complementary DNA.

The AIDS virus (HTLV-III, LAV) has been shown to be the causative agent of AIDS, and has been found to cause a similar disease in chimpanzees (see, e.g., Alter et al., *Science*, 226:549 (1984)).

Although a great deal of effort has recently been directed towards discovering an effective treatment for AIDS, no safe effective treatment has heretofore been described. There thus remains an urgent need for a method for inactivating the AIDS virus and for the treatment of AIDS.

SUMMARY OF THE INVENTION

In accordance with the present invention, a method for inactivating a virus having a lipid-containing capsid, such as an AIDS-causing virus, comprises contacting the virus with an inactivating amount of phosphatidyl choline. Such a virus can be inactivated in contaminated body fluids or derivatives thereof, such as blood or blood derivatives, by treating the body fluid or derivative with an inactivating amount of phosphatidyl choline. Acquired Immune Deficiency Syndrome in mammals is treated by administering a pharmaceutically effective amount of phosphatidyl choline to a mammal. In a preferred embodiment of this invention, the phosphatidyl choline is administered in the form of an Active Lipid (AL) composition or fraction as hereinafter defined.

DESCRIPTION OF THE PREFERRED EMBODIMENTS

Although the exact mechanisms of AIDS virus infection are not known, there are several contributing events to consider. The virus may activate a type of T-lymphocyte known as suppressor T-lymphocyte, which in turn, offset the role of another type of T-lymphocyte known as helper T-lymphocytes in fighting infectious agents through the production of suppression factors.

The relative depression of helper T-lymphocytes may reduce the effectiveness of an "immune surveillance" mechanism that destroys emergent microfoci of tumor cells. The clinical manifestations of AIDS are consistent with a suppression of helper T-lymphocytes, since the patient encounters multiple, virulent, opportunistic infections and, in some cases, develops a highly malignant tumor (Kaposi's Sarcoma).

A key event in the development of AIDS involves a highly specific lymphotropic effect of the AIDS virus, in which the virus binds to a surface receptor that is presented on the surface of helper T-lymphocytes, propagates in these cells and produces a cytopathic effect. The net result is the profound reduction of the helper T-lymphocyte population and its associated immune response.

It has surprisingly been discovered that viruses having a lipid-containing capsid, such as the AIDS virus, are inactivated by contacting the virus with an inactivating amount of phosphatidyl choline. Other viruses which may be amenable to inactivation by phosphatidyl choline include Friend Leukemia Virus, Feline Leukemia Virus, Rous Sarcoma Virus, Murine Mammary Tumor Virus, and the like.

Phosphatidyl choline is a common membrane fluidizer found in nature. However, when phosphatidyl choline is introduced into the blood system of mammals, it forms stable bi-layers or integrates into serum lipoproteins, both of which are slow in affecting membrane fluidity. As a result, when phosphatidyl choline alone is introduced into the bloodstream, most of it is degraded by the liver prior to having an opportunity to affect membrane fluidity. (Lyte and Shinitzky, unpublished results.)

Accordingly, in a preferred embodiment of this invention, phosphatidyl choline is administered in the form of an Active Lipid (AL) fraction which also contains phosphatidyl ethanolamine and neutral lipids. An AL composition comprising phosphatidyl choline can be derived from natural sources such as egg yolk and soybeans, as described in U.S. Pat. No. 4,474,773 (incorporated herein by reference).

AL has been found to inactivate viruses having a lipid-containing capsid, such as retroviruses including AIDS virus, in solution at AL concentrations greater than about 100 μg/ml. Preferably the concentration of AL in solution is greater than about 200 μg/ml for viral inactivation.

Retroviruses, such as AIDS virus, bud through an infected host cell membrane as a final step in packaging of mature virus capsids ready to infect new host cells. The mature virus capsid thus contains host membrane, which in turn contains lipids.

The rate of membrane fluidization by phosphatidyl choline can be markedly increased when phosphatidyl choline is integrated in structures which facilitate the process of lipid exchange. The formation of these structures is optimized by a particularly effective AL composition described in U.S. patent application Ser. No. 759,270, filed July 26, 1985 now abandoned, and is 233,555 and incorporated herein by reference. The AL composition therein described includes neutral lipids and phopholipids in about a 7:3 ratio by weight, respectively, with the phospholipids including phosphatidyl choline and phosphatidyl ethanolamine. Advantageously, the phospholipids are present in the AL composition in a ratio of about 2 parts by weight phosphatidyl choline and about 1 part by weight phosphatidyl ethanolamine, to provide an AL composition of about a 7:2:1 ratio by weight of neutral lipids, phosphatidyl choline and phosphatidyl ethanolamine, respectively (sometimes referred to herein as AL 721).

Phosphatidyl ethanolamine is a natural phospholipid which has been found to destabilize lipid bi-layers and can disintegrate stable phosphatidyl choline liposomes. However, mixtures of phosphatidyl choline and phosphatidyl ethanolamine alone tend to precipitate in aqueous solutions (e.g., blood).

A stable emulsion in an aqueous solution can be formed with a mixture of phosphatidyl choline, phosphatidyl ethanolamine and neutral lipids (predominantly glycerides). A stable emulsion of these lipids which is formed in an aqueous solution is comprised of a chylomicron-like assembly wherein the glycerides serve as a hydrophobic carrier on the surface of which the phosphatidyl choline and phosphatidyl ethanolamine molecules are randomly spread.

The neutral lipids of the lipid mixture may include monoglycerides, diglycerides, and triglycerides; however, it is preferable that triglycerides be present in a greater amount by weight than any other type of glyceride. It is particularly preferred that over 50% by weight of the glycerides are triglycerides.

AL 721 has proven effective in inactivating AIDS virus. Although the invention is described herein with reference to inactivation of the AIDS virus, it is to be understood that the invention is equally applicable to other viruses having lipid-containing capsids which are amenable to inactivation by the composition described herein.

Without being bound to any particular theory, it is believed that AL has a direct effect on the virus capsid, which is quite similar to the cell membrane of its host. HTLV-III, as a member of the retrovirus class, buds through its host cell membrane as a final step in the packaging of mature capsids ready to infect new host cells, as noted above. Thus, the AIDS virus capsid contains host membrane, which in turn, may be sensitive to fluidization by AL. The fluidization may have its effect on binding protein(s) in the capsid. Alternately, the fluidization may promote a disaggregation of the virus' supramolecular structure.

It is also possible that AL may function via a modulation of lymphocyte membrane microviscosity, altering the position or conformation of the receptor responsible for binding of HTLV-III.

The virucidal activity of AL on AIDS virus is demonstrated in the following examples, which are for illustrative purposes only and are not intended to be limiting. In the examples, a standard indicator cell line (H9) was used to test the effectiveness of AL 721 in inactivating HTLV-III virus, and to test AL 721 cytotoxicity, according to the procedures set forth in Popovic et al., Science, 224:497 (1984). The H9 line is unique, in that the cells are permissive for the HTLV-III virus, allow it to replicate and express key markers, yet the characteristic cytopathic effect (CPE) is largely inhibited. The H9 line thus allows for the production and study of the virus, in a stable cultured cell model of the infection. Example I also tests AL 721 inactivation of AIDS virus using Peripheral Blood Leucocytes. The correlation between AIDS virus inactivation with respect to the H9 cell line and AIDS virus inactivation with respect to a normal T-cell line has been demonstrated by Mitsuya et al., Science, 226:172 (1984).

In order to test the effectiveness of AL 721 on AIDS virus inactivation using the indicator cell line (H9) and Peripheral Blood Leucocytes, four measurements were made:

(1) Cell Number:

Though the cytopathic effect, or cell death, is greatly inhibited, there is still a reduction in the number of cells following infection. The reduction is one measure of the status of treated virus.

(2) p15 Protein Expression:

Antibody directed against one of the internal core proteins of HTLV-III p15 (a denotation which corresponds to a protein having a molecular weight of 15,000 daltons), is used to assay its expression in the infected cells.

(3) p24 Protein Expression:

Antibody directed against one of the internal core proteins, p24 (as above, protein of 24,000 molecular weight), is used to assay its expression in the infected cells.

(4) Reverse Transcriptase Expression:

As a retrovirus, HTLV-III replicates its RNA via a DNA intermediate, using an enzyme called reverse transcriptase (RNA-dependent DNA polymerase). As such, it is possible to quantitate the expression of HTLV-III by measuring the activity of this enzyme, within an indicator line that has been infected with the virus.

EXAMPLE I

AL 721, prepared as described in U.S. Ser. No. 759,270, filed July 26, 1985 (supra), now U.S. Ser. No. 232,555, in a solution of 2.5 mg AL 721 per ml solution (including 1% ethanol) was diluted to achieve the AL 721 concentrations indicated in Table 1 below. AL 721 and HTVL-III virus (or HTLV-III virus alone) was added to Peripheral Blood Leukocytes or H9 cells, to infect the cells and determine the effect of various concentrations of AL 721 on HTLV-III inactivation. The results are shown in Table 1 below.

TABLE 1
EFFECT OF SIMULTANEOUS ADDITION OF AL 721 AND HTLV-III VIRUS ON PERIPHERAL BLOOD LEUKOCYTES (PBL) AND H9 CELLS

| Treatment | PBL | | | H9 Cells | | |
|---|---|---|---|---|---|---|
| | RT | p15 | p24 | RT | p15 | p24 |
| HTLV-III (infected control) | 100% | 100% | 100% | 100% | 100% | 100% |
| AL 721 @ 20 μg/ml + HTLV-III | 77% | 67% | 50% | 107% | 73% | 100% |
| AL 721 @ 40 μg/ml + HTLV-III | 78% | 58% | 75% | 94% | 67% | 48% |
| AL 721 @ 100 μg/ml + HTLV-III | 32% | 50% | 50% | 75% | 47% | 48% |

EXAMPLE II

Example I was repeated in all essential details except that AL 721 was tested at levels of 50 μg/ml, 100 μg/ml, 200 μg/ml. Table 2A shows data on simultaneous administration while Table 2B shows comparative data on pre-treatment of virus with AL prior to infection of H9 cell.

TABLE 2A
Effect of Simultaneous Addition of AL 721 and HTLV-3 on H9 cells

| [AL 721] | Cell Count ($\times 10^{-5}$) | RT | p15 | p24 |
|---|---|---|---|---|
| (untreated) | 4.0 | 100% | 100% | 100% |
| 50 μg/ml | 3.9 | 100% | 100% | 100% |
| 100 μg/ml | 3.2 | 98% | 100% | 93% |
| 200 μg/ml | 2.8 | 94% | 92% | 79% |
| 400 μg/ml | 2.6 | 74% | 35% | 68% |

TABLE 2B
Effect of Pre-treatment of HTLV-3 by AL 721 in the H9 Cell Model

| [AL 721] | Cell Count ($\times 10^{-5}$) | RT | p15 | p24 |
|---|---|---|---|---|
| (untreated) | 4.0 | 100% | 100% | 100% |
| 50 μg/ml | 3.8 | 100% | 100% | 100% |
| 100 μg/ml | 3.3 | 90% | 77% | 79% |
| 200 μg/ml | 3.5 | 84% | 74% | 89% |
| 400 μg/ml | 1.9 | 67% | 74% | 55% |

The results in these tables demonstrate that AL can significantly inhibit the expression of key viral markers whether virus is pre-treated or simultaneously administrated with compound. The most significant reduction is seen in the core proteins—p15, p24 which exhibit 35% to 55% of control levels.

EXAMPLE III

Example I was repeated in all essential details except that AL 721 was tested at levels of from 100–1000 μg/ml on H9 cells only, and with or without the presence of ethanol in the AL 721 solution. The results are shown in Tables 3A and 3B below.

TABLE 3
ACTIVITY OF AL 721 AGAINST HTLV-III IN THE H9 CELL MODEL, WHEN SIMULTANEOUSLY ADMINISTERED (2 Formulations)

3A ETHANOL-FREE HOMOGENATE IN RPMI

| Treatment | Cell Count ($\times 10^{-5}$) | RT | p15 | p24 |
|---|---|---|---|---|
| HTLV-III (infected control) | 8.2 | 100% | 100% | 100% |
| AL 721 @ 100 μg/ml + HTLV-III | 8.4 | 82% | 52% | 56% |
| AL 721 @ 200 μg/ml + HTLV-III | 8.2 | 80% | 33% | 44% |
| AL 721 @ 500 μg/ml + HTLV-III | 8.1 | 77% | 28% | 27% |
| AL 721 @ 1000 μg/ml + HTLV-III | 8.6 | 70% | 15% | 11% |

3B 2.5 mg/ml AL 721 SOLUTION CONTAINING 1% ETHANOL (Diluted to levels shown below)

| Treatment | Cell Count ($\times 10^{-5}$) | RT | p15 | p24 |
|---|---|---|---|---|
| HTLV-III (infected control) | 8.0 | 100% | 100% | 100% |
| AL 721 @ 100 μg/ml + HTLV-III | 8.3 | 88% | 38% | 27% |
| AL 721 @ 200 μg/ml + HTLV-III | 8.6 | 78% | 23% | 25% |
| AL 721 @ 500 μg/ml + HTLV-III | 8.1 | 72% | 16% | 17% |
| AL 721 @ 1000 μg/ml + HTLV-III | 5.5 | 59% | 15% | 16% |

The results shown in Tables 3A and 3B demonstrate that AL 721 is capable of significantly inhibiting the expression of 2 key markers of HTLV-III infection (p15 and p24 core proteins), as well as inhibiting reverse transcriptase (RT) activity, with a regimen of simultaneous administration of drug and virus. Using p15 or p24 expression as a measure of inhibition of HTLV-III, it is believed that the $ID_{50}$ is about 100 μg/ml in the case of the AL 721 formulation without ethanol (Table 3A). Results with the ethanol formulation (Table 3B) may show a slight additive effect, with the $ID_{50} < 100$ μg/ml (i.e., without ethanol 52% of control p15, whereas the ethanol experiment produced 38% of control p15).

EXAMPLE IV

The cytotoxicity of AL 721 at the 1000 μg/ml level was tested using the H9 cell line only in the absence of HTLV-III infection against untreated control, with and without the presence of ethanol in solution. The results are shown in Table 4 below.

TABLE 4
CYTOTOXICITY OF AL 721 ON UNINFECTED CELLS
(Viability assessed by Trypan Blue Exclusion)

| [AL 721] | [Ethanol] | ($\times 10^{58}$) Cell Count | (%) Cell Count |
|---|---|---|---|
| — | — | 16.8 | 100% |
| 1000 μg/ml | — | 9 | 53% |

TABLE 4-continued

CYTOTOXICITY OF AL 721 ON UNINFECTED CELLS
(Viability assessed by Trypan Blue Exclusion)

| [AL 721] | [Ethanol] | ($\times 10^{58}$) Cell Count | (%) Cell Count |
|---|---|---|---|
| 1000 μg/ml | 0.5% | 5.9 | 35% |

The above results suggest that AL 721 is not acting primarily via an anti-metabolite mechanism of action (i.e., inhibition of viral reverse transcriptase). Moreover, these results suggest a model where virus capsid structure is disrupted either pre- or post-assembly.

The above examples indicate that AL 721 is capable of inactivating HTLV-III in the H9 test system, on the basis of four independently verifiable endpoints (i.e., cell numbers, [p15], [p24], [RT]). If a stable or perhaps metastable change in the T-lymphocyte membrane is invoked as a mechanism of action, pretreatment of cells with AL 721, following by its removal should also demonstrate a protective effect.

This data demonstrates that a AL inactivates AIDS virus. Because the development of AIDS disease in humans requires AIDS virus infection of many cells over a relatively long period of time, AL is suitable for administration to mammals for the treatment or prophylaxis of AIDS or pre-AIDS. Pre-AIDS refers to the prodromal stage of disease in which there is evidence of exposure to the virus (e.g., presence of antibodies in serum to HTLV-III or LAV) and in which one of the typical symptoms of disease is present (e.g., reduced T4/T8 cell ratio, lymphadenopathy, weight loss, appetite loss, etc.), but prior to profound loss of T-cell function and prior to the development of opportunistic infection or Kaposi's Sarcoma.

For the treatment or prophylaxis of AIDS in mammals, the AL mixture is administered to mammals in a pharmaceutical amount to achieve a concentration in the blood of AL of greater than about 100 μg/ml, preferably greater than about 200 μg/ml.

AL may be administered in a variety of dosage forms via enteral or parenteral routes. AL may, for example, be suspended in a pharmaceutically acceptable carrier such as saline, and administered to the mammals parenterally, e.g., by intravenous or intramuscular injection, intravenous infusion, or intraperitoneal injection for the treatment or prevention of AIDS. For parenteral administration, it is preferable to administer AL to mammals in amounts ranging from about 100-250 mg/kg body weight/day. In addition, the AL may be administered as a solid or semi-solid subcutaneous implant designed to slowly release the AL in therapeutic amounts.

The AL composition may also be orally administered to mammals in pharmaceutically acceptable carriers such as food materials (as a dietary supplement), as well as other forms of oral administration, as by means of tablets or capsules in known pharmaceutically acceptable carriers. When administering AL in the diet (using food as a carrier), it is preferable that the diet contains no other lipids in order to maximize the activity of the AL. Examples of dietary supplements containing AL include gelatin capsules and food bars. Additionally, AL can be packaged separately, for consumption after dissolving the mixture in a non-lipid liquid. AL can be orally administered to mammals in amounts within the range of from about 1-20 g/day, preferably within the range of from about 15-20 g/day.

For prophylactic use, AL is administered to mammals to prevent the development of AIDS in pre-AIDS patients or in high-risk patients.

AL is useful for AIDS virus inactivation or treatment or prophylaxis of AIDS in mammals when used in conjunction with other AIDS virus-inactivating or modulating agents, such as agents which are effective in reducing the reverse transcriptase activity of the AIDS virus or in immune modulation. Agents which are effective in reducing reverse transcriptase activity include Suramin, HPA-23, Foscarnet and the like. Immune modulators include lymphokines (such as interleukin-II), interferons and the like.

AL is also useful for topical administration to mammals as a virucidal agent to, for example, inactivate AIDS virus or other viruses in sexually transmitted body fluids, or to combat epidermal virus infections and the like. For topical administration, AL is administered in pharmaceutically effective amounts in carriers such as creams, salves, lubricants and the like, or in a patch.

The present invention provides an effective method for inactivating viruses having lipid-containing capsids, such as the AIDS retroviruses, and for the treatment or prophylaxis of AIDS or pre-AIDS in mammals. Since many modifications, variations and changes in detail may be made to the described embodiments, it is intended that all matter in the foregoing description be interpreted as illustrative and not in a limiting sense.

What is claimed is:

1. A method for inactivating a virus having a lipid-containing capsid, comprising contacting a virus having a lipid-containing capsid with an inactivating amount of a composition comprising neutral lipids, phosphatidyl choline and phosphatidyl ethanolamine; the neutral lipids comprising glycerides; the neutral lipids, phosphatidyl choline and phosphatidyl ethanolamine being present in the composition in proportions that provide formation of integrated structures of said composition, which structures promote lipid exchange with said capsid to inactivate the virus.

2. The method of claim 1 wherein the virus is a retrovirus.

3. The method of claim 1 wherein the virus is an Acquired Immune Deficiency Syndrome-causing virus in humans.

4. The method of claim 2 wherein the retrovirus is HTLV-III or LAV.

5. The method of claim 3 comprising contacting said virus with an inactivating amount of said composition, said method further comprising treating the virus with an inactivating amount of another AIDS virus-inactivating agent.

6. The method of claim 5 wherein said composition comprises about seven parts by weight neutral lipids, about two parts by weight phosphatidyl choline and about one part by weight phosphatidyl ethanolamine, the phosphatidyl choline, neutral lipids and phosphatidyl ethanolamine being present in the composition in proportions that provide formation of integrated structures of said AL composition, which structures promote lipid exchange with said capsid to inactivate the virus, wherein the neutral lipids comprise glycerides and the glycerides comprise over 50% by weight triglycerides.

7. A method for reducing the infectivity of an Acquired Immune Deficiency Syndrome-causing virus, comprising contacting an Acquired Immune Deficiency Syndrome-causing virus with an inactivating amount of an Active Lipid (AL) composition, said AL composition comprising neutral lipids, phosphatidyl choline, and phosphatidyl ethanolamine, the neutral lipids comprising glycerides, the phosphatidyl choline, neutral lipids and phosphatidyl ethanolamine being present in the composition in proportions that provide formation of integrated structures of said AL composition, which structures promote lipid exchange with said virus to inactivate the virus.

8. The method of claim 1, 2, 3, 4 or 7 wherein the composition comprises about seven parts by weight neutral lipids and about three parts by weight of a mixture including phosphatidyl choline and phosphatidyl ethanolamine in proportions that provide formation of integrated structures of said AL composition, which structures promote lipid exchange with said capsid to inactivate the virus.

9. The method of claim 8 wherein the composition comprises about seven parts by weight neutral lipids, about two parts by weight phosphatidyl choline and about one part by weight phosphatidyl ethanolamine.

10. The method of claim 9 wherein said glycerides comprises triglycerides.

11. The method of claim 10 wherein over 50% by weight of said glycerides are triglycerides.

12. The method of claim 11 wherein the virus is contacted with the AL composition in solution at an AL composition concentration of greater than about 100 µg/ml.

13. The method of claim 12 wherein the virus is contacted with the AL composition in solution at an AL composition concentration of greater than about 200 µg/ml.

14. The method of claim 12 wherein said solution is blood or a blood derivative.

15. The method of claim 13 wherein said solution is blood or a blood derivative.

16. The method of claim 10 wherein the composition is contained in a cream, salve, lubricant or patch for topical administration for mammals.

17. The method of claim 7 wherein the composition comprises about 7 parts by weight neutral lipids, about 2 parts by weight phosphatidyl choline, and about 1 part by weight phosphatidyl ethanolamine, wherein the neutral lipids comprise glycerides and the glycerides comprise over 50 percent by weight triglycerides.

18. A method for the treatment of Acquired Immune Deficiency Syndrome (AIDS) or pre-AIDS in a mammal in need of treatment for AIDS or pre-AIDS, or for the prophylaxis of AIDS or pre-AIDS, comprising administrating to said mammal a pharmaceutically effective amount of an (AL) composition to treat or prevent AIDS in said mammal, said (AL) composition comprising neutral lipids, phosphatidyl choline and phosphatidyl ethanolamine, the neutral lipids comprising glycerides, the phosphatidyl choline, neutral lipids and phosphatidyl ethanolamine being present in the composition in proportions that provide formation of integrated structures of said (AL) composition which structures promote lipid exchange with membrane material for the treatment of AIDS or pre-AIDS.

19. The method of claim 18 wherein the AL composition comprises about seven parts by weight neutral lipids and about three parts by weight of a mixture including phosphatidyl choline and phosphatidyl ethanolamine.

20. The method of claim 19 wherein the AL composition comprises about seven parts by weight neutral lipids, about two parts by weight phosphatidyl choline and about one part by weight ethanolamine.

21. The method of claim 20 wherein said glycerides comprise triglycerides.

22. The method of claim 21 wherein over 50% by weight of said glycerides are triglycerides.

23. The method of claim 22 wherein the AL composition is administered parenterally in a pharmaceutically acceptable carrier, in AL amounts within the range of from about 100–250 mg/kg body weight/day.

24. The method of claim 23 wherein the AL composition is administered orally in amounts within the range of from about 1–20 g/day.

25. The method of claim 22 wherein the AL composition is administered orally in amounts within the range of from about 15–20 g/day.

26. The method of claim 18 including administering to said mammals a pharmaceutically effective amount of another AIDS virus-inactivating agent.

27. The method of claim 26 wherein the phosphatidyl choline is present in an Active Lipid (AL) composition, said AL composition comprising about seven parts by weight neutral lipids, about two parts by weight phosphatidyl choline and about one part by weight phosphatidyl ethanolamine, wherein the neutral lipids comprise glycerides and the glycerides comprise over 50% by weight triglycerides.

28. A method of reducing the infectivity of a virus having a lipid-containing membrane, comprising increasing the fluidity of said membrane by contacting the virus with an infectivity-reducing amount of a composition comprising neutral lipids, phosphatidyl choline and phosphatidyl ethanolamine; the neutral lipids comprising glycerides; the neutral lipids, phosphatidyl choline and phosphatidyl ethanolamine being present in the composition in proportions that provide formation of integrated structures of said composition, which structures promote lipid exchange with said membrane to increase the fluidity of said membrane and reduce the infectivity of the virus.

29. The method of claim 28 wherein the composition comprises about seven parts by weight neutral lipids and about three parts by weight of a mixture including phosphatidyl choline and phosphatidyl ethanolamine in proportions that provide formation of integrated structures of said AL composition, which structures promote lipid exchange with said membrane to reduce the infectivity of the virus.

30. The method of claim 29 wherein the composition comprises about seven parts by weight neutral lipids, about two parts by weight phosphatidyl choline and about one part by weight phosphatidyl ethanolamine.

31. The method of claim 30 wherein said glycerides comprise triglycerides.

32. The method of claim 31 wherein over 50% by weight of said glycerides are triglycerides.

33. The method of claim 32 wherein the virus is contacted with the AL composition is solution at an AL composition concentration of greater than about 100 µg/ml.

34. The method of claim 33 wherein the virus is contacted with the AL composition in solution at an AL composition concentration of greater than about 200 g/ml.

35. The method of claim 33 wherein said solution is blood or a blood derivative.

36. The method of claim 34 wherein said solution is blood or a blood derivative.

* * * * *